United States Patent [19]

Raijmakers

[11] Patent Number: 5,739,363

[45] Date of Patent: Apr. 14, 1998

[54] ISOMERISATION OF EQUILIN

[75] Inventor: Petrus Hendricus Raijmakers, Uden, Netherlands

[73] Assignee: Akzo Nobel, N. V., Arnhem, Netherlands

[21] Appl. No.: 744,513

[22] Filed: Nov. 6, 1996

[30] Foreign Application Priority Data

Nov. 6, 1995 [EP] European Pat. Off. .............. 95202990

[51] Int. Cl.$^6$ ...................................................... C07J 1/00
[52] U.S. Cl. .......................................... 552/625; 552/630
[58] Field of Search ...................................... 552/630, 625

[56] References Cited

U.S. PATENT DOCUMENTS 5,395,831 3/1995 Gemmill, Jr. et al. .

OTHER PUBLICATIONS

E. Ayanoglu et al., *Tetrahedron*, 35:13:1591–1594, 1978.
J.C. Jacquesy et al., *Comptes Rendus Hebdomadaries des Seances de L'Academie des Sciences Chimiques*, 274:10:969–971, 1972.
J. Jacqusy et al., C.R. *Acad. Sc. Paris*, 274:10:969–971, 1972, France.
E. Ayanogglu et al., *Tetrahedron*, 35:1591–1594, 1979, Great Britain.

*Primary Examiner*—José G. Dees
*Assistant Examiner*—Barbara Badio
*Attorney, Agent, or Firm*—Mary E. Gormley

[57] ABSTRACT

The invention relates to a method of isomerisation of equilin or a derivative thereof to delta(8,9)-dehydro estrone [delta (8,9)DHE], characterized in that equilin or a derivative thereof is treated with a lithium salt of ethylenediamine or with lithium amide in dimethylsulfoxide.

12 Claims, No Drawings

ISOMERISATION OF EQUILIN

FIELD OF THE INVENTION

The invention relates to a method of isomerisation of equilin or derivatives thereof, more particularly to the isomerisation of equilin to 3-hydroxy-estra-1,3,5(10),8(9)-tetraen-17-one [delta(8,9)-dehydro estrone; delta(8,9)DHE; delta 8 estrone; 8,9 dehydro estrone; CAS no. 61612-83-7].

BACKGROUND OF THE INVENTION

The sulfate of the delta(8,9) derivative of equilin [delta (8,9)DHES] is present in minor amounts of about 3–4% in natural conjugated estrogen compositions, for instance in the commercially available product Premarin® which is being used in hormone replacement therapy. It has been suggested in SCRIP no. 2049 (1995), p. 15 that minor amounts of delta(8,9)DHES could have a significant contribution to the effect of conjugated estrogens. It has further been suggested that delta(8,9)DHES, which has a relatively low affinity to the estrogen receptor, has a high functional activity, which may play a role in the reported LDL-cholesterol-reducing properties and cardiovascular effects of conjugated estrogens, in particular of Premarin®. Data reveal that delta(8,9)DHES contributes about 18% of Premarin's circulating estrogens. It is therefore of importance to obtain an easy method of production for delta(8,9)DHE, which can easily be converted by methods known in the art to the sulfate of delta(8,9)DHES.

Apart from cumbersome total synthesis, J. C. Jacquesy et al., Chem. Abstr. 76 (1972), 154000f disclosed isomerisation of equilin in hyperacidic media. Conversion to delta(8,9) DHE was achieved by using hydrogen fluoride or hydrogen fluoride/antimony fluoride at −30° C. It is evident that such dangerous reaction conditions are completely unsuitable and unacceptable for large scale production of delta(8,9)DHE. Moreover, in U.S. Pat. No. 5,395,831, wherein the method of Jacquesy is applied, it has been disclosed that said hydrogen fluoride method does not provide pure delta(8,9) DHE, but in addition thereto 10% of the unwanted delta(9, 11)-isomer. Methods of production which are commercially acceptable, whether or not through isomerisation of equilin, thus have not been disclosed.

SUMMARY OF THE INVENTION

The present invention offers the first easy and inexpensive method of production of delta(8,9)DHE, through isomerisation of equilin or a derivative thereof to said derivative, characterized in that equilin or a derivative thereof is treated with a lithium salt of ethylenediamine or with lithium amide in dimethylsulfoxide.

The general formula of equiline and said derivatives is indicated in Formula I:

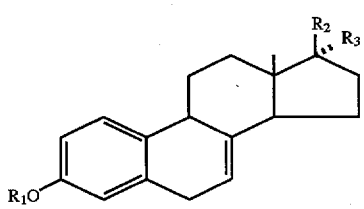

wherein $R_1$ is H, alkyl, acyl or silyl(alkyl)$_3$; $R_2$ is H and $R_3$ is OH, O-acyl, O-alkyl or O-silyl (alkyl)$_3$ or $R_3$ is H and $R_2$ is OH, O-acyl, O-alkyl or O-silyl (alkyl)$_3$; or $R_2$ and $R_3$ together represent O; or $R_2$ and $R_3$ together represent acetal or cyclic acetal. $R_1$ might also represent a substituted alkyl such as e.g. methoxy ethoxy methyl.

According to the isomerization method of the present invention derivatives of the general formula II can be prepared:

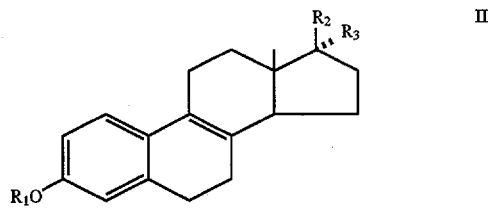

wherein $R_1$, $R_2$ and $R_3$ have the previously defined meaning.

DETAILED DESCRIPTION OF THE INVENTION

In a preferred embodiment the isomerisation is performed using lithium salts of ethylenediamine, since this method results into the production of very pure delta(8,9)DHE. Such lithium salts can be prepared by treatment of ethylenediamine with lithium or with alkyllithium, preferably with methyllithium. (Co)solvents like tetrahydrofuran, dimethylsulfoxide, and the like may be added. Usually mixtures of delta(8,9)DHE and equilin or derivatives thereof are obtained when (co)solvents are added. Lithium amide in dimethylsulfoxide (DMSO) also provides mixtures of delta (8,9)DHE and equiline or derivatives thereof, which can be converted as such into their sulfates, to be used in the manufacture of pharmaceutical compositions containing conjugated estrogens.

The term alkyl, as used in the definition of formula I, means a branched or unbranched alkyl group having preferably 1–6 carbon atoms, like hexyl, isobutyl, tertiary butyl, propyl, isopropyl, ethyl, and, preferably, methyl. The term acyl means an acyl group derived from an alkylcarboxylic acid, the alkyl moiety having the meaning given previously, or derived from formic acid. Acetals are derived from alcohols having preferably 1–6 carbon atoms.

When C3-esters of equilin are used, common esters such as esters of aliphatic carboxylic acids with 1–6 carbon atoms or simple aromatic carboxylic acids are preferred. Examples are esters of formic acid, acetic acid, propionic acid, benzoic acid and the like. Esters of acetic acid and benzoic acid are preferred. Under the reaction conditions applied, the esters are usually simultaneously saponified and the free delta(8, 9)DHE or a mixture thereof with equilin is obtained. If necessary, the reaction product can further be saponified using methods generally known in the art.

If in the compound of formula I, $R_1$ is silyl(alkyl)$_3$ the derivatives will also be hydrolyzed during the reaction resulting in compounds according to formula II wherein $R_1$ is H. Similarly, if $R_2$ or $R_3$ is O-acyl or silyl(alkyl)$_3$, compounds can be isolated wherein $R_2$ or $R_3$ is OH.

Preferably, the isomerisation is performed at a temperature of between about 0° and 90° C., and with more preference at about 30° C. if equiline or a derivative thereof is treated with a lithium salt of ethylenediamine or about 65° C. if equiline or a derivative thereof is treated with lithium amide in dimethylsulfoxide.

The conditions of isomerisation according to this invention are unobvious. The most straightforward method of isomerisation appears to be treatment of equilin under acidic conditions, for instance with acetic acid, hydrochloric acid, trifluorosulfonic acid, boron trifluoroetherate, or combinations thereof in solvents such as methanol, ethanol, tetrahydrofuran or toluene. However, under none of these conditions suitable results were obtained, since no reaction at all occurred or an intractable mixture of compounds was obtained.

Isomerisation under catalytic conditions (for instance palladium/carbon/benzyl alcohol) neither led to suitable results. The same holds for isomerisation under most of the alkaline conditions. Obvious methods such as isomerisation with butyllithium/potassium tert-butoxide, sodium amide, potassium tert-butoxide or sodium hydride in the usual solvents, lithium amide in dimethylformamide, sodium or potassium in ethylenediamine, and lithium in various amines, among which diisobutylamine, pentylamine, dimethylethylenediamine, piperazine, and piperidine, were virtually completely unsuccessful. Under the best conditions only 2 to 8% of desired material was obtained in an intractable mixture of various isomers, unknown reaction products, and starting material. Surprisingly only isomerisation using lithium in ethylenediamine, which afforded 95% of delta(8,9)DHE and lithium amide in DMSO, which afforded a mixture of about 55% of delta(8,9)DHE and 45% of starting material (equilin) which mixture can be used as such, appears to be successful. It is believed that these unique conditions provide a rare, if not the only possibility to obtain directly in a commercially available manner delta (8,9)DHE from equilin.

The following examples are illustrative for the invention and should in no way be interpreted as limiting the scope of the invention.

EXAMPLE 1

Lithium (13 g) was added portionwise to 920 ml of ethylenediamine under an atmosphere of nitrogen at 95° C. and the mixture was stirred for 30 min at 100° C. The reaction mixture was cooled to 23° C., after which 100 g of equilin were added at a temperature of ≦30° C. The mixture was stirred for another 2 h at 30° C. The suspension was poured into 2.5 l of ice water and at a temperature ≦25° C. acetic acid was added until pH 7. The aqueous layer was extracted three times with 2.5 l of ethyl acetate. The organic layer was washed with water, 5 g of active carbon (Norit®) were added and the suspension was stirred at 21° C. for 30 min. The suspension was filtered over dicalite and the filtrate was evaporated under vacuo until a volume of about 500 ml. The suspension was stirred for 1 h at 0° C., after which the crystalline material was filtered off, washed with ethyl acetate and dried under vacuo at 40° C., to obtain 81 g of delta(8,9)-dehydro estrone, having a purity of about 95%.

The contents of delta(8,9)DHE and equiline were determined using $^1$H-NMR spectroscopy, characteristic peaks of which are 0.90 ppm (C18) for delta(8,9)DHE and 5.53 ppm (C7) and 0.79 ppm (C18) for equilin.

EXAMPLE 2

Lithium amide (5 g) was added to a mixture of 5 g of equilin in 150 ml of DMSO. The mixture was heated to 65° C. and stirred for 70 min. The reaction mixture was poured into 500 ml of water and acidified to pH 6.5 using 4N hydrochloric acid. The crystals were filtered off, washed with water and dried under vacuo at 40° C. to obtain 5 g of a 4:5 mixture of equilin and delta(8,9)-dehydro estrone.

EXAMPLE 3

A 6% solution of methyllithium-lithiumbromide complex in diethylether (23.5 ml) was added during approximately 15 minutes to 46 ml ethylenediamine under an atmosphere of nitrogen at a temperature of approximately 25° C. The temperature of the mixture was raised to 55° C. and diethylether was distilled off. Subsequently the reaction mixture was stirred for 1 h at 55° C. The mixture was cooled to 20° C. and 2.5 g of equilin was added. The mixture was stirred for another 90 minutes at 30° C.

The suspension was poured into ice water and the mixture was extracted with ethyl acetate. After evaporation of the ethyl acetate extract until a volume of 20 ml was reached and cooling to 0° C., 2 g of crystalline delta 8-estrone was isolated.

EXAMPLE 4

Lithium (1,1 g) was added portionwise to 80 ml of ethylenediamine under an atmosphere of nitrogen at 100° C. and the mixture was stirred for 30 min at 100° C. The reaction mixture was cooled to 23° C., after which 4 g of 17β-dihydroequilin were added at a temperature of ≦30° C. The mixture was stirred for another 4 h at 30° C. The suspension was poured into 250 ml of ice water and at a temperature of ≦25° C. acetic acid was added until pH 7. The suspension was cooled to 5° C. and the crystals were filtered off. The crystals were suspended in 150 ml of water and 100 ml of ethyl acetate were added. The layers were separated and the ethyl acetate solution was evaporated under vacuo until a volume of 20 ml. The suspension was stirred at −15° C. for 1 h, after which the crystals were filtered off, washed with ethyl acetate and dried under vacuo at 40° C., to obtain 2.5 g of 8,9-dehydro-17β-estradiol, having a purity of >95%.

EXAMPLE 5

A solution of methyllithium-lithiumbromide (20 ml, 2.1M) in diethylether was added in 10 min to 40 ml of ethylenediamine under an atmosphere of nitrogen at 36° C. The temperature of the mixture was raised to 55° C. and diethylether was distilled off. The mixture was stirred for 1 h at 55° C. The reaction mixture was cooled to 3° C., after which 2 g of equilin-3-methylether were added at a temperature of ≦10° C. The mixture was stirred for another 2 h at 12° C., after which 200 ml of ice water were added. To the mixture acetic acid was added until pH 8. The suspension was stirred for 1 h at 15° C., after which the crystals were filtered off, washed with water and dried under vacuo at 45° C., to obtain 2.0 g of 8,9-dehydro-estrone-3-methylether, having a purity of approx. 80%.

EXAMPLE 6

According to the procedure described in example 5, 17β-dihydroequilin 3,17-diacetate, was treated with methyllithium/ethylenediamine at 30° C. to give quantitavely 8,9-dehydro-17β-estradiol having a purity of approx. 90%.

EXAMPLE 7

According to the procedure described in example 4, equilin-17-neopentylacetal was treated with lithium/ ethylenediamine at 20° C. to give in a yield of 90% 8,9-dehydro-estron-17-neopentylacetal having a purity of approx. 90%.

EXAMPLE 8

According to the procedure described in example 4, 17β-dihydroequilin-3,17-di(trimethylsilylether) was treated with lithium/ethylenediamine to give quantitavely 8,9-dehydro-17β-estradiol having a purity of approx. 90%.

I claim:

1. A method for the isomerisation of equilin or a derivative thereof according to the general formula I:

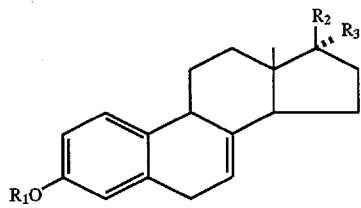

wherein $R_1$ is H, alkyl, acyl or silyl(alkyl)$_3$; $R_2$ is H and $R_3$ is OH, O-acyl, O-alkyl or O-silyl(alkyl)$_3$, or $R_3$ is H and $R_2$ is OH, O-acyl, O-alkyl or O-silyl(alkyl)$_3$, or $R_2$ and $R_3$ together represent O, or $R_2$ and $R_3$ together represent acetal or cyclic acetal;

to delta(8,9)-dehydro estrone or a derivative thereof, said method comprising treating equilin or the derivative thereof with a lithium salt of ethylenediamine or with lithium amide in dimethylsulfoxide.

2. The method according to claim 1, wherein $R_1$ is acyl and $R_2$ and $R_3$ together represent O.

3. The method according to claim 1, wherein equiline or a derivative thereof is treated with a lithium salt of ethylenediamine.

4. The method according to claim 1, wherein the reaction temperature is from about 0° C. to about 90° C.

5. The method according to claim 4, wherein the reaction temperature is about 30° C. and equilin or a derivative thereof is treated with a lithium salt of ethylenediamine.

6. The method of claim 2, wherein equilin or a derivative thereof is treated with a lithium salt of ethylenediamine.

7. The method of claim 2, wherein the reaction temperature is from about 0° C. to about 90° C.

8. The method of claim 3, wherein the reaction temperature is from about 0° C. to about 90° C.

9. The method according to claim 4, wherein the reaction temperature is about 65° C. and equilin or a derivative thereof is treated with lithium amide in dimethylsulfoxide.

10. The method of claim 7, wherein the reaction temperature is about 30° C. and equilin or a derivative thereof is treated with a lithium salt of ethylenediamine.

11. The method of claim 7, wherein the reaction temperature is about 65° C. and equilin or a derivative thereof is treated with lithium amide in dimethylsulfoxide.

12. The method of claim 8, wherein the reaction temperature is about 30° C.

* * * * *